United States Patent [19]

Pohl et al.

[11] Patent Number: 5,235,078
[45] Date of Patent: Aug. 10, 1993

[54] HETEROCYCLIC ORGANOMETALLIC COMPOUNDS

[75] Inventors: Ludwig Pohl; Martin Hostalek; Matthias Lokai, all of Darmstadt, Fed. Rep. of Germany

[73] Assignee: Merck Patent Gesellschaft mit Beschrankter Haftung, Darmstadt, Fed. Rep. of Germany

[21] Appl. No.: 626,054

[22] Filed: Dec. 12, 1990

[30] Foreign Application Priority Data

Dec. 12, 1989 [DE] Fed. Rep. of Germany ....... 3941005
Mar. 23, 1990 [DE] Fed. Rep. of Germany ....... 4009394

[51] Int. Cl.$^5$ ............................................. C07F 5/06
[52] U.S. Cl. .......................................... 556/1; 556/27; 556/64
[58] Field of Search ....................................... 556/1, 27

[56] References Cited

U.S. PATENT DOCUMENTS 4,268,455 5/1981 Langer et al. ........................ 556/1

OTHER PUBLICATIONS

Beachley et al. J. Inorg. Chem., 14(10), 2534–7, 1975.
Clark et al. J. Organometallic Chemistry, 13(1) 61–71, 1968.

*Primary Examiner*—Mukund J. Shah
*Assistant Examiner*—Y. N. Gupta
*Attorney, Agent, or Firm*—Millen, White, Zelano & Branigan

[57] ABSTRACT

The invention relates to heterocyclic organometallic compounds formula I below and to the use thereof for the production of thin films and layers on substrates by gas phase deposition.

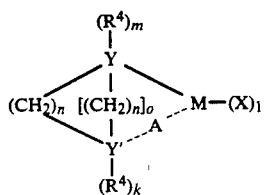

4 Claims, No Drawings

HETEROCYCLIC ORGANOMETALLIC COMPOUNDS

BACKGROUND OF THE INVENTION

The invention relates to heterocyclic organometallic compounds containing aluminum, gallium or indium as metals, and to the use thereof for the production of thin films or expitaxial layers by gas phase deposition.

The deposition of such layers either from pure elements of the third group or from combinations with other elements, such as, for example, gallium arsenide, indium phosphide or gallium phosphide, can be used to produce electrical, dielectric, electronic, optical and optoelectronic structural and circuit elements, compound semiconductors and lasers. The deposition of these layers takes place from the gas phase.

The properties of these films depend on the deposition conditions and the chemical composition of the film deposited.

All the known methods such as the metal-organic chemical vapor deposition (MOCVD) method, the metal-organic molecular beam epitaxy (MOMBE) method, the photo-metal-organic vapor phase (photo-MOVP) method in which the substances are decomposed by the UV irradiation, the laser-chemical vapor deposition (laser-CVD) method or the metal-organic magnetron sputtering (MOMS) method, are suitable for deposition from the gas phase. The advantages over other methods are a controllable layer growth, a precise doping control and also simple handling and production-friendliness resulting from the normal-pressure or low-pressure conditions. Such other methods which deposit from the liquid phase are, e.g., electrochemical deposition or high vacuum methods such as electron sputtering.

In the MOCVD method, organometallic compounds are used which decompose to deposit the metal at a temperature below 1100° C. Typical apparatuses currently used for MOCVD comprise a "bubbler" having a feed for the organometallic component, a reaction chamber which contains the substrate to be coated, and also a carrier gas source which should be inert towards the organometallic compound. The "bubbler" is kept at a constant, relatively low temperature which is preferably above the melting point of the organometallic compound, but far below the decomposition temperature. The reaction chamber or decomposition chamber is preferably at a very much higher temperature, below 1100° C, at which the organometallic compound decomposes completely and the metal is deposited. The organometallic compound is converted to the vapour state by the carrier gas and is passed through a lock into the decomposition chamber together with the carrier gas. The mass flow rate of the vapor can readily be controlled, and a controlled growth of the thin layers is consequently also possible.

Hitherto, metal alkyls such as, for example, trimethyl gallium, trimethyl aluminium or trimethyl indium, have mainly been used for gas phase deposition. These compounds are, however, extremely sensitive to air, spontaneously ignitible and in some cases decomposable even at room temperature. Elaborate safety measures are therefore necessary for the production, transportation, storage and application of these compounds. A few, somewhat more stable, adducts of the metal alkyls with Lewis bases such as, for example, trimethylamine and triphenylphosphine, are also known (described, for example, in GB 2,123,422, EP-A 108,469 or EP-A 176,537), but these are only suitable to a limited extent for gas phase deposition owing to their low vapour pressure.

Organometallic compounds suitable for the MOCVD technique are known from German Offenlegungsschrift 3,631,469. However, the compounds described therein do not contain any compounds in which the element of the IIIrd and Vth group of the periodic system, that is to say the acceptor atom and the donor atom, are covalently linked.

It was therefore the object of the present invention to find organometallic compounds which are easy to handle and are stable at room temperature and which have a sufficiently high vapour pressure to enable them to be decomposed from the gas phase, that is to say are suitable for the various methods of gas phase deposition.

It has now been found that organometallic compounds containing the acceptor atom of the IIIrd group and two donor atoms of the Vth group in a cyclic arrangement in which either one of the donor atoms is covalently linked and the other is linked to the acceptor atom via a donor-acceptor interaction or both donor atoms are linked covalently to the acceptor atom, are outstandingly suitable for gas phase deposition.

Compared with the organometallic compounds hitherto used and known, these heterocyclic organometallic compounds have the decisive advantage that an additional intramolecular stabilization takes place by electron transfer from the donor atoms to the electron-deficient acceptor atom. The presence of at least two donor atoms thus increases the stability.

Surprisingly, in spite of this increased stability, the compounds according to the invention have sufficiently high vapour pressures to enable them to be decomposed from the gas phase.

SUMMARY OF THE INVENTION

The invention therefore relates to the heterocyclic organometallic compounds of the formula

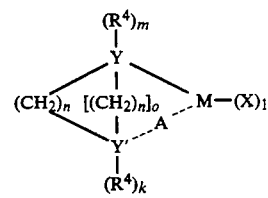

wherein

M is aluminium, gallium or indium,

Y and Y' are each nitrogen, phosphorus or arsenic, n is in each case 2, 3 or 4, (independently chosen)

m is 0 or 1.

o is 0 or 1, m+o is 1, l is 1 or 2,

A is a covalent bond between Y' and M if l=1, or a donor-acceptor interaction between Y' and M if l=2, k is 0, 1 or 2, subject to the provisions that, in the event that l=1 and o=1, k=0, in the event that l=2 and o=1, k=1, in the event that l=1 and o=0, k=1 and, in the event that l=2 and o=0, k=2, X is $R^3$, $-(CHR^5)_p-Z$ in which p=1, 2, 3, 4 or 5, it also being possible for p to be 0 in the event that Z=F or perfluoroalkyl, o—$(CH_2)_r$—$C_6H_4$—$(CH_2)_s$—Z,
1,2—$(CH_2)_r$—$C_6H_{10}$—$(CH_2)_s$—Z,
1,2—$(CH_2)_r$—$C_6H_8$—$(CH_2)_s$—Z,
1,2—$(CH_2)_r$—$C_6H_6$—$(CH_2)_s$—Z,
1,2—$(CH_2)_r$—$C_5H_8$—$(CH_2)_s$—Z,
1,2—$(CH_2)_r$—$C_5H_6$—$(CH_2)_s$—Z,
1,2—$(CH_2)_r$—$C_5H_4$—$(CH_2)_s$—Z or
1,2—$(CH_2)_r$—$C_4H_6$—$(CH_2)_s$—Z, is $-NR^1R^2$, $-PR^1R^2$, $-AsR^1R^2$, —F or perfluoroalkyl having up to 7 C atoms, r and s independently of one another are each 0, 1, 2 or 3, $R^1$, $R^2$, $R^3$ and $R^4$ independently of one another are each H, an alkyl or alkenyl group having up to 8 C atoms, it being possible for these groups to be partially or completely fluorinated, a cycloalkyl or cycloalkenyl group having 3-8 C atoms or an aryl group, and $R^5$ is in each case H or an alkyl group having up to 4 C atoms and which can also be partially or completely fluorinated, subject to the proviso that, in the event that M=aluminium, l=1 and X=$R^3$, $R^3$ is then methyl, an alkyl or alkenyl group having 3-8 C atoms, it being possible for these groups to be partly or completely fluorinated, a cycloalkyl or cycloalkenyl group having 3-8 C atoms or an aryl group.

Another subject of the invention is the use of the compounds of the formula I as starting materials for the production of thin films or epitaxial layers by gas phase deposition and to a process for the production of thin films or epitaxial layers by gas phase deposition from organometallic compounds, in which the compounds of the formula I are employed as the organometallic compounds. It is also a subject of the invention that one or more compounds of arsenic, antimony or phosphorus which are gaseous under the reaction conditions used are supplied during the deposition process in the process according to the invention.

By virtue of their at least twofold intramolecular stabilization, the compounds according to the invention have a high stability to air and oxygen. They are not spontaneously ignitible and are hence easy to handle.

In the gas phase, however, the compounds according to the invention can readily be decomposed with the deposition of the metal. Since the compounds of the formulae I and II contain stable and easily eliminable detachable groups, the result is a lower incorporation of carbon, which has great advantages for the quality of the end products.

The films deposited can be formed on any desired substrates either as pure IIIB element or as combinations with elements of the Vth group or other elements, depending on the process variant. Depending on the substrate and the deposition technique, they can have an epitaxial nature.

The compounds of the formula I have a vapor pressure suitable for the MOCVD technique and are therefore outstandingly suitable for use as starting materials.

The formula I comprises two different groups of compounds of the formula Ia (for l=1) and Ib (for l=2).

The subformula Ia

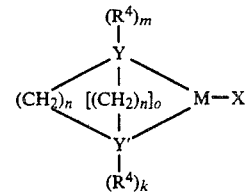

wherein $R^4$, m, n, Y, Y', o, k, M and X have the meaning indicated embraces compounds in which the acceptor atom M is connected via covalent bonds to two donor atoms. In formula Ia, therefore, A in formula I is in this case a covalent bond if l=1.

The subformula Ib

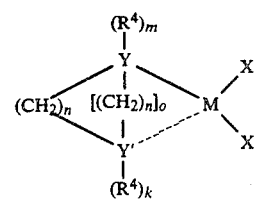

wherein Y', M, Y, R., m, n, o, k and X have the meaning indicated embraces compounds in which l=2, that is to say two groups X are attached to the metal atom, and a donor-acceptor interaction therefore takes place between Y' and M, and only one donor atom Y is linked covalently. Here too, however, a cyclic arrangement containing one acceptor atom and two donor atoms is formed. A in formula Ib thus corresponds to a donor-acceptor interaction between Y' and M.

In formulae I, Ia and Ib M is aluminium (Al), gallium (Ga) or indium (In), preferably Ga or In.

Y and Y' in these formulae can be identical or different. Preferably, they have the same meaning and are nitrogen, phosphorus or arsenic, preferably nitrogen.

If l is 2, the two X radicals can also be identical or different.

The radicals $R^1$, $R^2$, $R^3$ and $R^4$ in the formulae I, Ia and Ib are in each case preferably a linear or branched alkyl group having 1-8 C atoms, preferably 1-5 C atoms. The alkyl groups are preferably linear and, accordingly, are preferably methyl, ethyl, propyl, butyl, pentyl and also hexyl, heptyl, octyl, isopropyl, sec.-butyl, tert.-butyl, 2-methylpentyl, 3-methylpentyl or 2-octyl. The alkyl radicals can be partly or completely fluorinated and are, for example, monofluoromethyl, trifluoromethyl, difluoroethyl, trifluoroethyl, pentafluoroethyl, hexafluoroisopropyl or trifluoropropyl.

If $R^1$, $R^2$, $R^3$ and/or $R^4$ are a cycloalkyl or cycloalkenyl group having 3-8 C atoms, they are preferably cyclopropyl, cyclobutyl, cyclopentyl, cyclopentenyl, cyclohexyl, cyclohexenyl, cyclohexadienyl, cycloheptyl, cycloheptenyl, cycloheptadienyl, cyclooctyl, cyclooctenyl, cyclooctadienyl, cyclooctatrienyl or cyclooctatetraenyl.

$R^1$, $R^2$, $R^3$ and/or $R^4$ are also preferably alkenyl groups having 3-8 C atoms, preferably 3-5 C atoms. Accordingly, they are preferably propenyl, butenyl, pentenyl and also hexenyl, heptenyl or octenyl.

Compounds which are also preferred are those of the above formulae wherein $R^1$, $R^2$, $R^3$ and/or $R^4$ is an aryl group. In this respect aryl is preferably synonymous with a phenyl group. This phenyl group can also be substituted. Since these substituents exert no appreciable effect on the end use desired, any substituents which have no interfering effect on the decomposition reaction are allowable.

The two radicals $R^4$ in the formulae I, Ia and Ib can have identical or different meanings.

n is 2, 3 or 4, preferably 2 or 3. m and o are each 0 or 1, m+o being 1.

If M is aluminium, l is 1 and X is $R^3$, $R^3$ is then preferably an alkyl or alkenyl group having 3–8 C atoms, it being possible for these groups to be partly or completely fluorinated, a cycloalkyl or cycloalkenyl group having 3–8 C atoms or an aryl group, the preferred meanings already indicated applying to all these groups.

X in the formulae I, Ia and Ib is preferably $R^3$, with the preferred meanings indicated for $R^3$ or is —(CHR$^5$)$_p$—Z. p is preferably 2, 3 or 4. If Z is fluorine or a perfluoroalkyl group, p can also be 0.

$R^5$ is either an H atom or an alkyl group having up to 4 C atoms which can be partly or completely fluorinated. Accordingly, $R^5$ is preferably H, methyl, ethyl, propyl, butyl, trifluoromethyl, pentafluoroethyl, monofluoromethyl or difluoromethyl.

Preferably, if p>1, only one of the $R^5$ radicals is an alkyl group having the preferred meanings indicated. The other $R^5$ radicals present are then preferably H.

X is also preferably o-(CH$_2$)$_r$—C$_6$H$_4$—(CH$_2$)$_s$—Z, 1,2-(CH$_2$)$_r$—C$_6$H$_{10}$—(CH$_2$)$_s$—Z, 1,2-(CH$_2$)$_r$—C$_5$H$_8$—(CH$_2$)$_s$—Z or 1,2-(CH$_2$)$_r$—C$_4$H$_6$—(CH$_2$)$_s$—Z wherein r and s are each 0, 1 or 2. These are substituted aryl or cyclic structures.

Primarily, Z is preferably —NR$^1$R$^2$, F or perfluoroalkyl having, preferably, up to 4 C atoms, and, accordingly, is preferably trifluoromethyl, pentafluoroethyl, heptafluoropropyl, hexafluoroisopropyl or nonafluorobutyl. As a second preference, Z is —PR$^1$R$^2$ or —AsR$^1$R$^2$. The compounds according to the invention can therefore also contain 3 or 4 donor atoms in the molecule. $R^1$ and $R^2$ then have the preferred meanings indicated.

Accordingly, the following groupings (1)–(17) are particularly preferred for X:

| -alkyl | -phenyl | -cyclohexyl | —F | -perfluoralkyl |
|--------|---------|-------------|-----|----------------|
| (1) | (2) | (3) | (4) | (5) |

—(CH$_2$)$_p$—Z    —(CH$_2$)$_3$—NR$^1$R$^2$    —(CHR$^5$)$_p$—NR$^1$R$^2$
(6)                (7)                        (8)

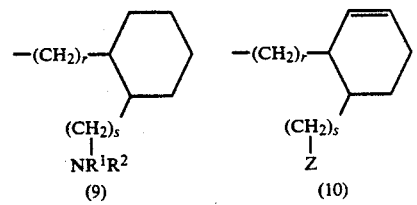

(9)              (10)

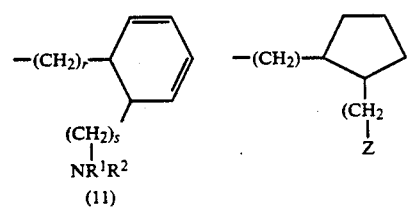

(11)

-continued

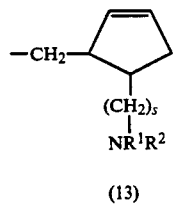    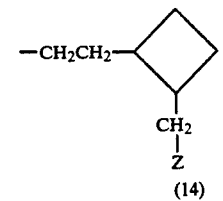

(13)                     (14)

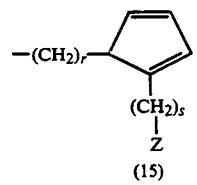    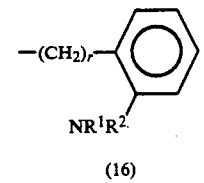

(15)                     (16)

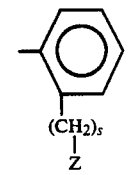

(17)

Whenever X contains the group Z, a further intramolecular stabilization takes place as a result of electron transfer from the nitrogen, phosphorus, fluorine or arsenic to the element M.

Formula Ia embraces, for example, the following subformalae Iae-Iaf, which are particularly preferred.

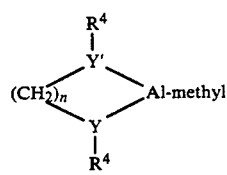

Iaa

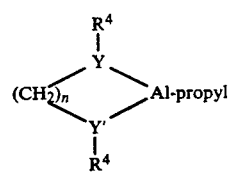

Iab

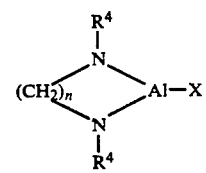

Iac

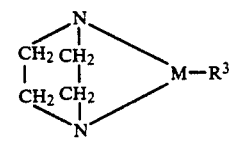

Iad

-continued
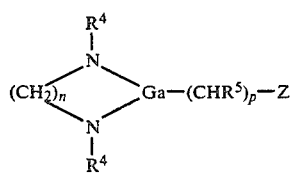 Iae
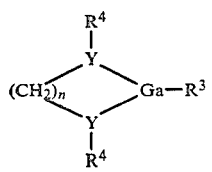 Iaf
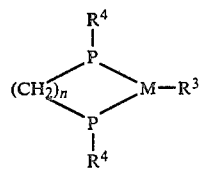 Iag
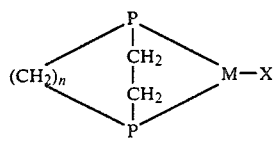 Iah
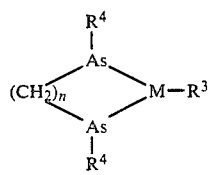 Iai
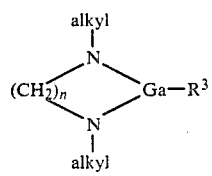 Iaj
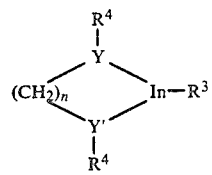 Iak
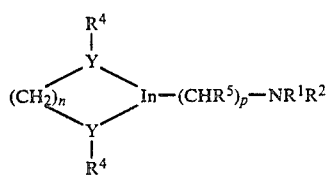 Ial
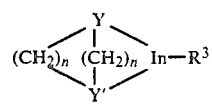 Iam
-continued
Ian
Iao
Iap
Iaq
The following groups of the formulae Iba–Ibl are particularly preferred representatives of the formula Ib:
Iba
Ibb
Ibc
Ibd
Ibe -continued

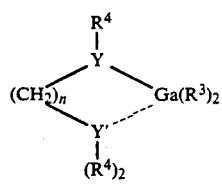

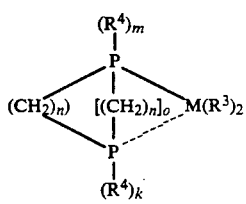

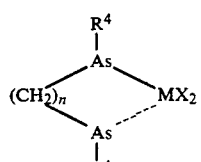

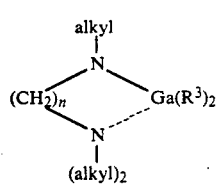

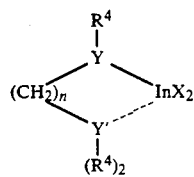

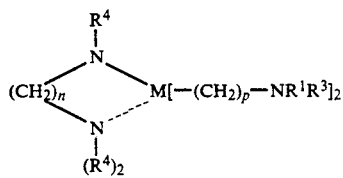

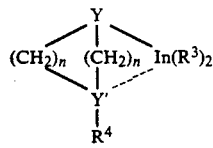

The compounds of the formula I are outstandingly suitable for MOCVD epitaxy or the MOCVD method, since they decompose at elevated temperatures with the liberation of the corresponding metal. They are also suitable for the other methods of gas phase decomposition, such as photo-MOVP, laser-CVD or MOMS.

The compounds of the formula I are prepared by methods known per se, such as are described in the literature (for example G. Bähr, P. Burba, Methoden der organischen Chemie ("Methods of Organic Chemistry"), volume XIII/4, Georg Thieme Verlag, Stuttgart (1970)), specifically under reaction conditions which are known and suitable for the reactions mentioned. In this regard it is also possible to make use of variants known per se but not mentioned in detail here.

Ibf  Thus compounds of the formula I can, in general, be prepared by reacting the corresponding metal halide derivative with an alkali metal organyl of the desired Lewis base or with a Grignard compound in an inert solvent.

Ibg  The reactions are preferably carried out in inert solvents. Solvents suitable in this respect are any solvents which do not disturb the reaction and do not interfere in its course. The reaction conditions correspond essentially to those known from the literature for the preparation of similar compounds.

In the process according to the invention for the preparation of thin films or epitaxial layers on any desired substrate, the stabilized organometallic adduct compounds of the formula I are employed as starting compounds in the gas phase deposition processes,
Ibh  known per se, of organometallic compounds. The reaction conditions can be selected by analogy with the values known from the literature and familiar to those skilled in the art.

In order to produce compound semiconductors, electrical, dielectric, electronic, optical and optoelectronic systems, one or more compounds, which are gaseous
Ibi  under the reaction conditions used, of arsenic antimony or phosphorus, for example AsH$_3$, As(CH$_3$)$_3$, PH$_3$ or SbH$_3$, can be added, in addition, during the deposition process in the decomposition chamber in the process according to the invention. A further variant of the process according to the invention consists in adding dopants in addition to the organometallic adducts according to the invention of the formula I, during the
Ibj  deposition process. In this connection, volatile organometallic compounds of iron, magnesium, zinc or chromium are employed as dopants. Zn(CH$_3$)$_2$, Mg(CH$_3$)$_2$ or Fe(C$_5$H$_5$)$_2$, for example, rank as preferred compounds in this regard.

It is also possible to add the compounds of the formula I as dopants during the deposition process of other
Ibk  organometallic compounds.

The layers produced by the processes according to the invention can be used to produce electrical, dielectric, electronic, optical and optoelectronic structural and circuit elements, compound semiconductors or lasers.

Since, in the epitaxial systems at present in use, for
Ibl  thermodynamic reasons only approximately 1-10 % of the free metal alkyls used can be deposited as an epitaxial layer on the substrate, the destruction of the excess metal alkyls, which cannot be recovered owing to their extreme sensitivity, represents a considerable problem. Owing to their high stability, the compounds of the formula I according to the invention, on the other hand, open up new possibilities for the safe destruction or for the recovery of the valuable III B compounds.

The following examples are intended to illustrate the invention in greater detail, without limiting it. Temperature data are quoted in degrees centigrade or Kelvin. m.p. means melting point and b.p. means boiling point.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 41 005.6, filed Dec. 12, 1989 and German P 30 09 394.8, filed Mar. 23, 1990, are hereby incorporated by reference.

Temperature data are quoted in degrees centigrade or Kelvin, m.p. means melting point and b.p. means boiling point.

EXAMPLES

Example 1

25.5 g (0.15 mol) of ethylgallium dichloride in 100 ml of n-hexane are added, at $-20°$, to 14.6 g (0.15 mol) of dilithium N,N'-dimethylethylenediamide in 300 ml of n-hexane. The mixture is stirred at room temperature for 2 hours and filtered, and the filtrate is concentrated. Sublimation at a bath temperature of 220° and a vacuum of $10^{-1}$ mbar gives 2,5-dimethyl-1-ethyl-2,5-diaza-1-gallacyclopentane as a colourless solid, stable in air.

CH analysis:

|  | found | calculated |
|---|---|---|
| C | 39.09 | 38.97 |
| H | 8.08 | 8.18 |

Structure:
$$\begin{array}{c} CH_3 \\ | \\ CH_2-N \\ \phantom{CH_2-N}\backslash \\ \phantom{CH_2-N\backslash}Ga-C_2H_5 \\ \phantom{CH_2-N}/ \\ CH_2-N \\ | \\ CH_3 \end{array}$$

The following are prepared analogously:
2,5-dimethyl-1-methyl-2,5-diaza-1-gallacyclopentane
2,5-dimethyl-1-propyl-2,5-diaza-1-gallacyclopentane
2,5-diethyl-1-ethyl-2,5-diaza-1-gallacyclopentane
2,5-diethyl-1-butyl-2,5-diaza-1-gallacyclopentane
2,5-diethyl-1-methyl-2,5-diaza-1-gallacyclohexane
2,5-dimethyl-1-ethyl-2,5-diaza-1-gallacyclohexane
2,5-dimethyl-1-ethyl-2,5-diaza-1-indacyclohexane
2,5-dimethyl-1-ethyl-2,5-diaza-1-indacyclopentane
2,5-diethyl-1-ethyl-2,5-diaza-1-indacyclohexane
2,5-diethyl-1-ethyl-2,5-diaza-1-indacyclopentane
2,5-dimethyl-1-propyl-2,5-diaza-1-indacyclohexane
2,5-dipropyl-1-methyl-2,5-diaza-1-indacyclohexane
2,5-dimethyl-1-phenyl-2,5-diaza-1-gallacyclohexane
2,5-dimethyl-1-methyl-2,5-diaza-1-aluminacyclohexane
2,5-dimethyl-1-methyl-2,5-diaza-1-aluminacyclopentane
2,5-diethyl-1-pentyl-2,5-diaza-1-aluminacyclopentane
2,5-diethyl-1-pentyl-2,5-diaza-1-aluminacyclohexane
2,5-diphenyl-1-methyl-2,5-diaza-1-gallacyclohexane
2-ethyl-5-methyl-1-ethyl-2,5-diaza-1-gallacyclohexane
2,5-dimethyl-1-ethyl-2,5-diaza-1-indacycloheptane
2,5-diethyl-1-methyl-2,5-diaza-1-gallacycloheptane

Example 2

16.8 g (0.075 mol) of 3-dimethylaminopropylgallium dichloride (obtainable by reacting 3-dimethylaminopropyl-1-magnesium chloride with gallium trichloride) in 75 ml of THF are added, at $-20°$ C., to 7.4 g (0.075 mol) of dilithium N,N'-dimethylethylenediamide in 150 ml of THF.

The mixture is stirred for a further hour, allowed to stand at room temperature overnight and concentrated to one half, 100 ml of n-hexane are added and the mixture is filtered and the solvent is removed in vacuo. Sublimation in vacuo ($10^{-1}$ mbar) at a bath temperature of 220° C. gives 2,5-dimethyl-1-(3-dimethylaminopropyl)-2,5-diaza-1-gallacyclopentane.

The following are prepared analogously
2,5-dimethyl-1-(3-dimethylaminopropyl)-2,5-diaza-1-gallacyclohexane
2,5-dimethyl-1-(3-dimethylaminopropyl)-2,5-diaza-1-gallacycloheptane
2,5-dimethyl-1-(3-diethylaminopropyl)-2,5-diaza-1-gallacyclopentane
2,5-dimethyl-1-(3-diethylaminopropyl)-2,5-diaza-1-gallacyclohexane
2,5-dimethyl-1-(3-diethylaminopropyl)-2,5-diaza-1-gallacycloheptane
2,5-diethyl-1-(3-dimethylaminopropyl)-2,5-diaza-1-gallacyclohexane
2,5-diethyl-1-(3-dimethylaminopropyl)-2,5-diaza-1-gallacyclopentane
2,5-diethyl-1-(3-dimethylaminopropyl)-2,5-diaza-1-gallacycloheptane
2,5-diethyl-1-(4-dimethylaminobutyl)-2,5-diaza-1-gallacyclohexane
2,5-diethyl-1-(4-dimethylaminobutyl)-2,5-diaza-1-gallacyclopentane
2,5-diethyl-1-(4-dimethylaminobutyl)-2,5-diaza-1-gallacycloheptane
2-ethyl-5-propyl-1-(4-dimethylaminobutyl)-2,5-diaza-1-gallacyclohexane
2-ethyl-5-propyl-1-(4-dimethylaminobutyl)-2,5-diaza-1-gallacyclopentane
2-ethyl-5-propyl-1-(4-dimethylaminobutyl)-2,5-diaza-1-gallacycloheptane
2,5-dimethyl-1-(3-diphenylaminopropyl)-2,5-diaza-1-gallacyclohexane
2,5-dimethyl-1-(3-diphenylaminopropyl)-2,5-diaza-1-gallacyclopentane
2,5-dimethyl-1-(3-diphenylaminopropyl)-2,5-diaza-1-gallacycloheptane
2,5-dimethyl-1-(3-dimethylaminopropyl)-2,5-diaza-1aluminacyclopentane
2,5-dimethyl-1-(3-dimethylaminopropyl)-2,5-diaza-1-aluminacyclohexane
2,5-dimethyl-1-(3-dimethylaminopropyl)-2,5-diaza-1-aluminacycloheptane
2,5-dimethyl-1-(3-diethylaminopropyl)-2,5-diaza-1-aluminacyclopentane
2,5-dimethyl-1-(3-dimethylaminopropyl)-2,5-diaza-1-aluminacyclohexane
2,5-dimethyl-1-(3-dimethylaminopropyl)-2,5-diaza-1-aluminacycloheptane
2,5-diethyl-1-(3-dimethylaminopropyl)-2,5-diaza-1-aluminacyclohexane
2,5-diethyl-1-(3-dimethylaminopropyl)-2,5-diaza-1-aluminacyclopentane
2,5-diethyl-1-(3-dimethylaminopropyl)-2,5-diaza-1-aluminacycloheptane
2,5-diethyl-1-(4-dimethylaminobutyl)-2,5-diaza-1-aluminacyclohexane
2,5-diethyl-1-(4-dimethylaminobutyl)-2,5-diaza-1-aluminacyclopentane
2,5-diethyl-1-(4-dimethylaminobutyl)-2,5-diaza-1-aluminacycloheptane
2-ethyl-5-propyl-1-(4-dimethylaminobutyl)-2,5-diaza-1-aluminacyclohexane
2-ethyl-5-propyl-1-(4-dimethylaminobutyl)-2,5-diaza-1-aluminacyclopentane 2-ethyl-5-propyl-1-(4-dimethylaminobutyl)-2,5-diaza-1-aluminacycloheptane
2,5-dimethyl-1-(3-diphenylaminopropyl)-2,5-diaza-1-aluminacyclohexane
2,5-dimethyl-1-(3-diphenylaminopropyl)-2,5-diaza-1-aluminacyclopentane
2,5-dimethyl-1-(3-diphenylaminopropyl)-2,5-diaza-1-aluminacycloheptane
2,5-dimethyl-1-(3-dimethylaminopropyl)-2,5-diaza-1-indacyclopentane
2,5-dimethyl-1-(3-dimethylaminopropyl)-2,5-diaza-1-indacyclohexane
2,5-dimethyl-1-(3-dimethylaminopropyl)-2,5-diaza-1-indacycloheptane
2,5-dimethyl-1-(3-diethylaminopropyl)-2,5-diaza-1-indacyclopentane
2,5-dimethyl-1-(3-diethylaminopropyl)-2,5-diaza-1-indacyclohexane
2,5-dimethyl-1-(3-diethylaminopropyl)-2,5-diaza-1-indacycloheptane
2,5-diethyl-1-(3-dimethylaminopropyl)-2,5-diaza-1-indacyclohexane
2,5-diethyl-1-(3-dimethylaminopropyl)-2,5-diaza-1-indacyclopentane
2,5-diethyl-1-(3-dimethylaminopropyl)-2,5-diaza-1-indacycloheptane
2,5-diethyl-1-(4-dimethylaminobutyl)-2,5-diaza-1-indacyclohexane
2,5-diethyl-1-(4-dimethylaminobutyl)-2,5-diaza-1-indacyclopentane
2,5-diethyl-1-(4-dimethylaminobutyl)-2,5-diaza-1-indacycloheptane
2-ethyl-5-propyl-1-(4-dimethylaminobutyl)-2,5-diaza-1-indacyclohexane
2-ethyl-5-propyl-1-(4-dimethylaminobutyl)-2,5-diaza-1-indacyclopentane
2-ethyl-5-propyl1-(4-dimethylaminobutyl)-2,5-diaza-1-indacycloheptane
2,5-dimethyl-1-(3-diphenylaminopropyl)-2,5-diaza-1-indacyclohexane
2,5-dimethyl-1-(3-diphenylaminopropyl)-2,5-diaza-1-indacyclopentane
2,5-dimethyl-1-(3-diphenylaminopropyl)-2,5-diaza-1-indacycloheptane.

Example 3

14 g of diethylgallium chloride in 60 ml of n-hexane are added slowly, at room temperature and under an atmosphere of argon, to 9.7 g of lithium-N,N,N'-trimethylethyleneamide in 100 ml of n-hexane. When the reaction is complete, the LiCl is filtered off and rinsed three times with n-hexane, and the filtrate is subjected to fractional distillation in vacuo. After the removal of the solvent, diethylgallium 2-dimethylaminoethylmethylamide distils over at 126° C./0.4 mbar.

The following are prepared analogously:
dimethylgallium 2-dimethylaminoethylmethylamide
dimethylgallium 2-diethylaminoethylmethylamide
diethylgallium 2-diethylaminoethylmethylamide
diethylgallium 2-dimethylaminoethylethylamide
dipropylgallium 2-dimethylaminoethylmethylamide
dimethylgallium 3-dimethylaminopropylmethylamide
dimethylaluminium 2-dimethylaminoethylmethylamide
diethylaluminium 2-diethylaminoethylmethylamide
diethylaluminium 2-dimethylaminoethylpropylamide
dimethylaluminium 3-dimethylaminopropylmethylamide
diphenylaluminium 2-diethylaminoethylmethylamide
methyl 3dimethylaminopropylaluminium 2-dimethylaminoethylmethylamide
bis-(3-dimethylaminopropyl)-gallium 3-dimethylaminopropylmethylamide
dimethylindium 2-dimethylaminoethylmethylamide
diethylindium 3-diethylaminopropylmethylamide
diphenylindium 2-diethylaminoethylmethylamide
dipropylindium 2-dimethylaminoethylethylamide.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A heterocyclic, organometallic compound of the formula Ia

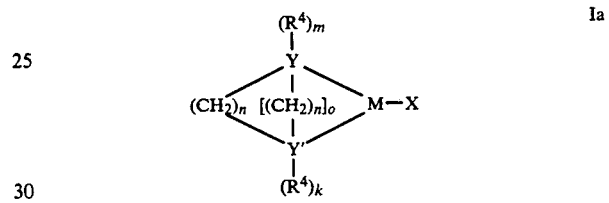

wherein
M is aluminum, gallium or indium;
Y and Y' are each nitrogen;
n is in each case 2, 3 or 4;
m is 0 or 1;
o is 0;
k is o or 1, subject to the proviso that where o=1, then k=o, and where o=0, then k=1;
X is $R^3$ or —$(CHR^5)_p$—Z, where p=1, 2, 3, 4 or 5 and p can also be 0 where Z=F or perfluoroalkyl, or substituted aryl and cyclic structures of the formulae:
—o—$(CH_2)_r$—$C_6H_4$—$(CH_2)_s$—Z,
—1,2—$(CH_2)_r$—$C_6H_{10}$—$(CH_2)_s$—Z,
—1,2—$(CH_2)_r$—$C_6H_8$—$(CH_2)_s$—Z,
—1,2—$(CH_2)_r$—$C_6H_6$—$(CH_2)_s$—Z,
—1,2—$(CH_2)_r$—$C_5H_8$—$(CH_2)_s$—Z,
—1,2—$(CH_2)_r$—$C_5H_6$—$(CH_2)_s$—Z,
—1,2—$(CH_2)_r$—$C_5H_4$—$(CH_2)_s$—Z,
—1,2—$(CH_2)_r$—$C_4H_6$—$(CH_2)_s$—Z;
Z is —$NR^1R^2$, $PR^1R^2$-$ASR^1R^2$, —F or perfluoroalkyl having up to 7 C atoms;
r and s independently of one another are each 0, 1, 2 or 3;
$R^1$, $R^2$, $R^3$ and $R^4$ independently of one another are each H, an alkyl or alkenyl group having up to 8 C atoms and fluorinated derivatives thereof, a cycloalkyl or cycloalkenyl group having 3–8 C atoms or an aryl group, and
$R^5$ is in each case H or an alkyl group having up to 4 C atoms and fluorinated derivatives thereof,
subject to the proviso that, in the event that M=aluminum, and X=$R^3$, $R^3$ is then methyl, an alkyl or alkenyl group having 3–8 C atoms or fluorinated derivatives thereof, a cycloalkyl or cycloalkenyl having 3–8 C atoms or an aryl group.

2. A heterocyclic, organometallic compound of formula Ia of claim 1, wherein

X is alkyl, phenyl, cyclohexyl, —F, perfluoroalkyl, —(CH$_2$)$_p$—Z, —(CH$_2$)$_3$—NR$^1$R$^2$ or —(CHR$^5$)$_p$—NR$^1$R$^2$, wherein p, R$^1$, R$^2$ and Z are as defined in claim 1.

3. A heterocyclic organometallic compound of formula Ia of claim 1, wherein

M is aluminum, o=0, k32 1 and

X is methyl, propyl or —(CH$_2$)$_3$—NR$^1$R$^2$, where R$^1$ and R$^2$ are as defined in claim 1.

4. A heterocyclic, organometallic compound of formula Ia of claim 1, wherein

M is gallium or indium, o=0, k=1 and X is R$^3$ or —(CHR$^5$)$_p$—NR$^1$R$^2$, wherein R$^1$, R$^2$, R$^3$ and R$^5$ are as defined in claim 1.

* * * * *